United States Patent [19]

Kogure et al.

[11] 3,965,161

[45] June 22, 1976

[54] PROCESS OF PRODUCING A 2-(4-ALKYLPHENYL)-PROPIONIC ACID

[75] Inventors: Katsura Kogure; Kunio Nakagawa, both of Kawagoe, Japan

[73] Assignee: Nisshin Flour Milling Co., Ltd., Tokyo, Japan

[22] Filed: Jan. 25, 1974

[21] Appl. No.: 436,633

[30] Foreign Application Priority Data

Jan. 29, 1973   Japan.............................. 48-11167

[52] U.S. Cl. ...................... 260/523 R; 260/515 R; 260/599; 424/308
[51] Int. Cl.² .................. C07C 63/52; C07C 51/24
[58] Field of Search ............ 260/503 R, 515 R, 171, 260/599, 523 R

[56] References Cited
UNITED STATES PATENTS 3,435,075   3/1969   Glamkowski et al. .............. 260/599

FOREIGN PATENTS OR APPLICATIONS 1,160,725   8/1969   United Kingdom ............. 260/523 R

OTHER PUBLICATIONS

Shiner et al., J. Am. Chem. Soc., *84* 4824 (1962).
Ghosal, C.A. *64* 8525f, (1969).
March, Advanced Organic Chemistry, McGraw Hill Book Co., (1968), p. 309.
Ex parte Jama, 18 J.P.O.S. 654–655.

*Primary Examiner*—Anton H. Sutto
*Attorney, Agent, or Firm*—James C. Haight

[57] ABSTRACT

A new process of producing a 2-(4-alkylphenyl)-propionic acid known as a valuable anti-inflammatory agent is now provided, which comprises treating an alkyl 3-methyl-3-(4-alkylphenyl)-glycidate with an acid to produce 2-(4-alkylphenyl)-propionaldehyde and 3-methyl-3-(4-alkylphenyl)-pyruvic acid through a new reaction, and then oxidising these intermediate products to the desired 2-(4-alkylphenyl)-propionic acid. This new process is operable in a facile way, gives a high yield of the desired product and is suitable for a commercial practice.

10 Claims, No Drawings

PROCESS OF PRODUCING A 2-(4-ALKYLPHENYL)-PROPIONIC ACID

This invention relates to a new process for producing a 2-(4-alkylphenyl)-propionic acid.

2-(4-lower alkylphenyl)-propionic acids and their pharmaceutically acceptable derivatives are known to have a high anti-inflammatory activity and have widely been used in the treatment of diseases associated with inflammation, such as rheumatism. Of the known 2-(4-alkylphenyl)-propionic acids, 2-(4-isobutylphenyl)-propionic acid is most useful for this therapeutic purpose.

It is known that the synthesis of a 2-(4-alkylphenyl)-propionic acid of the formula (I):

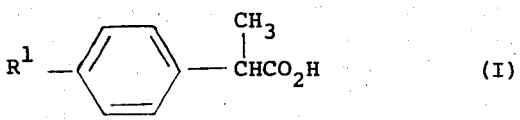

wherein $R^1$ stands for a lower alkyl group of 2–4 carbon atoms can be conducted by various methods described in the specifications of Japanese patent publication No. 7491/65, No. 22297/68 and No. 24550/72. However, all these prior art methods suffer from some drawback and are not very suitable for the production of the 2-(4-alkylphenyl)-propionic acid on a commercial scale.

Thus, according to the method of the Japanese patent publication No. 7491/65 (British patent No. 971,700), a 4-alkylacetophenone of the formula (V):

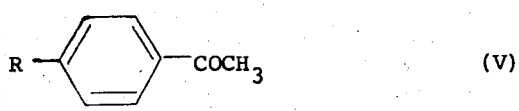

wherein R is an alkyl group is used as a starting compound and is converted into the desired 2-(4-alkylphenyl)-propionic acid of the formula (I) via six reaction stages. This known method involves many stages of reaction and is accordingly not advantageous for the commercial production of the desired compound of the formula (I).

According to the method of Japanese patent publication No. 22297/68 (British patent No. 971,700), a 4-alkylphenylethane derivative of the formula (VI):

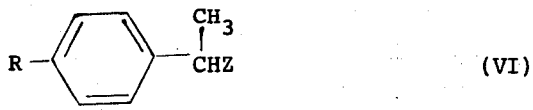

wherein R stands for an alkyl group and Z stands for a nitrile radical or a carboxylic acid ester radical is hydrolysed to give a corresponding 2-(4-alkylphenyl)-propionic acid of the formula (I). This known method suffers from the drawback that the starting compound of the formula (VI) is difficult to prepare and hence is very expensive.

According to the method of Japanese patent publication No. 24550/72 (British patent No. 1,160,725), a glycidic ester of the formula (II):

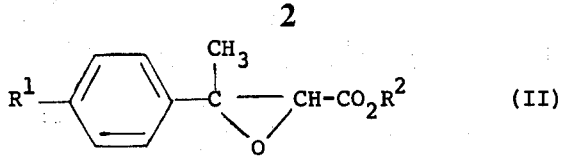

wherein $R^1$ represents an alkyl group of 2–4 carbon atoms and $R^2$ represents an alkyl group of 1–4 carbon atoms is used as the starting compound and is hydrolysed in the presence of an alkali metal hydroxide to give an alkali metal glycidate of the formula (VII):

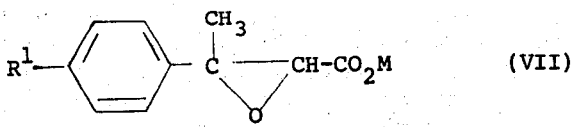

wherein $R^1$ has the same meaning as set out above and M represents an alkali metal, which is, in turn, treated with an acid to produce a propionaldehyde derivative of the formula (III):

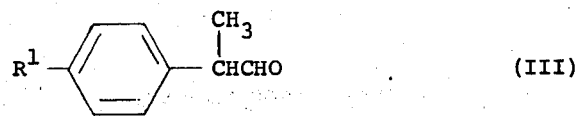

wherein $R^1$ has the same meaning as described above. The propionaldehyde derivative of the formula (III) is then oxidised to yield the desired 2-(4-alkylphenyl)-propionic acid of the formula (I). This known method is not suitable for the commercial production of the aimed product (I) because the intermediate product of the formula (VII) is unstable and gives the compound of the formula (III) only in a low yield so that the overall yield of the final product (I) is accordingly poor.

An object of this invention is to provide a new process for the production of 2-(4-alkylphenyl)-propionic acids which can be operated in a facile way and give the desired product in a high yield and which is suitable for use on a commercial scale. Further objects of this invention will be clear from the following description.

We have made our extensive research to achieve the above-mentioned purposes. As a result of our research, we have now found that when a 3-methyl-3-(4-alkylphenyl)-glycidic acid alkyl ester of the formula (II):

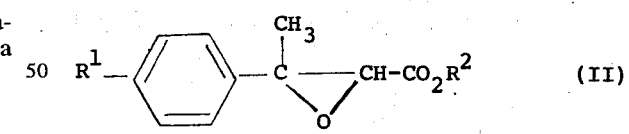

wherein $R^1$ and $R^2$ have the same meanings as defined above is treated with an aqueous mineral acid such as hydrochloric acid or sulfuric acid, there are directly formed the 2-(4-alkylphenyl)-propionaldehyde of the formula (III):

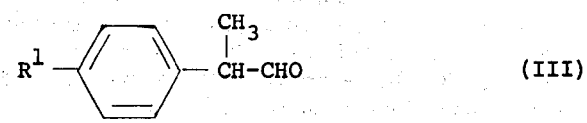

wherein $R^1$ has the same meaning as described above and the 3-methyl-3-(4-alkylphenyl)-pyruvic acid of the formula (IV):

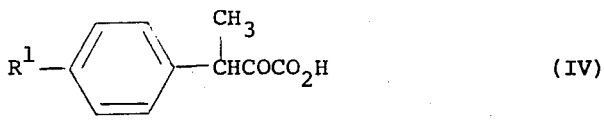

(IV)

wherein R[1] has the same meaning as described above in favorably high yields, and the 3-methyl-3-(4-alkylphenyl)-pyruvic acid of the formula (IV) is readily oxidisable to the desired 2-(4-alkylphenyl)propionic acid of the formula (I). The conversion of the glycidic ester of the formula (I) into the two products, namely the 2-(4-alkylphenyl)propionaldehyde of the formula (III) and the 3-methyl-3-(4-alkylphenyl)-pyruvic acid of the formula (IV) through a single-stage treatment of said glycidic ester with an acid, is a new reaction, which is not known as far as we are aware.

According to this invention, there is provided a new process of producing a 2-(4-alkylphenyl)propionic acid of the formula (I):

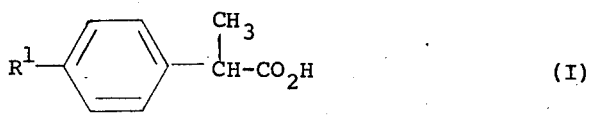

(I)

wherein R[1] stands for an alkyl group of 2-4 carbon atoms, or a pharmaceutically acceptable salt thereof, which comprises treating a 3-methyl-3-(4-alkylphenyl-glycidic acid ester of the formula (II):

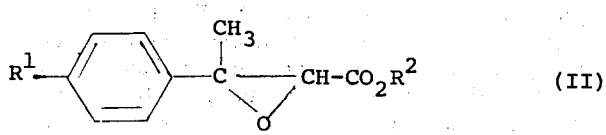

(II)

wherein R[1] has the same meaning as defined above and R[2] stands for an alkyl group of 1-3 carbon atoms with an acid to produce a 2-(4-alkylphenyl)-propinaldehyde of the formula (III):

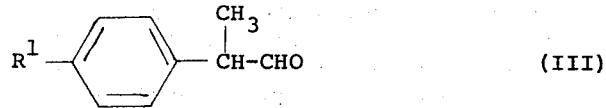

(III)

wherein R[1] has the same meaning as defined above, and a 3-methyl-3-(4-alkylphenyl)-pyruvic acid of the formula (IV):

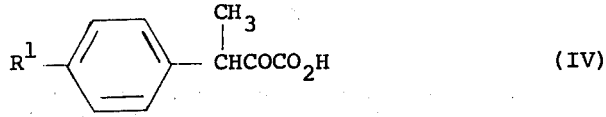

(IV)

wherein R[1] has the same meaning as defined above, and then oxidising the compound of the formula (III) and the compound of the formula (IV) to give the desired compound of the formula (I) or a salt thereof.

According to this invention, the compounds of the formulae (III) and (IV) may be produced directly in one stage by the treatment of the starting glycidate compound of the formula (II) with an aqueous mineral acid. This acid treatment can be carried out very easily and gives the intermediate products of the formulae (III) and (IV) in high yields. The subsequent oxidation of the intermediate products (III) and (IV) can also be carried out easily using a known oxidising agent. The process of this invention is thus operated in a facile way and gives the desired 2-(4-alkylphenyl)-propionic acid in an improved yield, and it requires one less reaction stage than in known method of the Japanese patent publication No. 24550/72. Accordingly, the process of this invention is well suitable for the commerical production of 2-(4-alkylphenyl)-propionic acids.

In the first stage of the process according to this invention, the starting glycidate compound of the formula (II) is treated with an aqueous mineral acid at an elevated temperature to produce the aldehyde compound of the formula (III) and the keto-acid compound of the formula (IV). The acid available for this purpose may suitably be a mineral acid such as hydrochloric acid and sulfuric acid. When a lower aliphatic acid, notably an alkanoic acid of 2-4 carbon atoms such as acetic acid, propionic acid and butyric acid, is present in the reaction mixture, the reaction can proceed very smoothly, and hence it is advantageous that such a lower aliphatic acid be employed as the reaction medium in which the reactants are dissolved. The acid treatment may suitably be carried out at a reaction temperature of 80°-140°C for a reaction time of about 1 hour. By changing the kind of the ester group R[2] in the starting glycidate compound (II), it is possible to vary the proportion of the aldehyde compound (III) to the pyruvic-acid compound (IV) produced. As the aldehyde compound (III) is a neutral substance and the keto-acid compound (IV) is an acidic substance, they are very easily separated from each other in a known manner. Each of these intermediate products (III) and (IV) may be isolated in a relatively pure form and may be used in the subsequent oxidising stage of the process without purification.

In the second stage of the process, the aldehyde compound of the formula (III) may be oxidised to the desired compound of the formula (I) by treating with a known oxidising agent such as silver oxide or potassium permanganate. Silver oxide may preferably be used in alkaline reaction conditions which are provided by the presence of an alkali metal hydroxide such as sodium hydroxide. Potassium permanganate may suitably be used in acidic reaction conditions, for example, in the presence of aqueous sulfuric acid. The pyruvic acid compound (IV) may be oxidised to the desired compound of the formula (I) by treating with a known oxidising agent such as hydrogen peroxide in an alkaline aqueous solution containing an alkali metal hydroxide such as sodium hydroxide or potassium hydroxide. When hydrogen peroxide is used as the oxidising agent, the oxidisation of the pyruvic acid compound (IV) may suitably be carried out at a reaction temperatue of 10°-25°C for a reaction time of 10-20 hours. When the oxidation step of the process is carried out in the presence of an alkali metal hydroxide, the 2-(4-alkylphenyl)-propionic acid oxidation product of the formula (I) is formed as an alkali metal salt (carboxylate) thereof. This salt may readily be converted into the free acid form by treating with a mineral acid such as hydrochloric acid or sulfuric acid if necessary. The final product of the formula (I) which is produced according to the process of this invention is of a high purity, and it may easily be further purified, if desired, by recrystallisation from petroleum benzine. Furthermore, the 2-(4-alkylphenyl)-propionic acid of the formula (I) in the free acid form may be converted into its pharmaceutically acceptable inorganic salt (carboxylate) such as the sodium, potassium or calcium salt, or into its pharmaceutically acceptable addition salt with an organic salt base such as benzylamine or triethylamine.

In known method of the Japanese patent publication No. 24550/72, the aldehyde compound of the formula (III) is produced in two stages from the glycidic alkyl ester compound of the formula (II) by hydrolysing said glycidic alkyl ester compound in alkaline conditions and then oxidising the resulting alkali metal glycidiate compound of the formula (VII). In contrast, according to this invention, the aldehyde compound of the formula (III) is produced directly from the glycidic alkyl ester compound of the formula (II) in one stage by treating said glycidic alkyl ester compound under acidic conditions, and it is evident that the hydrolysis stage of the above known method is omitted in the process of this invention. Accordingly, the process of this invention has the advantage that the required reaction stages are reduced by one, as compared to the known method of the Japanese patent publication No. 24550/72. In addition, the acid-treatment step of the process of this invention enables the starting compound (I) to be converted in one stage into the two intermediate products (III) and (IV) in high yields, respectively, so that the overall yield of the desired 2-(4-alkylphenyl)-propionic acid (I) is improved in the process of this invention, as compared to the known method of the Japanese patent publication No. 24550/72.

The 3-methyl-3-(4-alkylphenyl)-glycidic acid alkyl ester of the formula (II) which is employed as the starting compound in the process of this invention may be prepared, for example, in the following way: An acetophenone derivative of the formula (VIII):

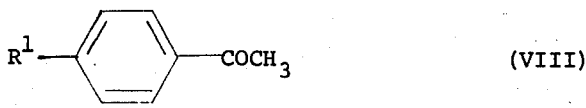

wherein $R^1$ is an alkyl group of 2–4 carbon atoms is reacted with an α-haloacetic acid acid ester of the formula (IX):

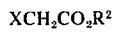

XCH$_2$CO$_2$R$^2$      IX.

wherein $R^2$ is an alkyl group of 1–3 carbon atoms and X is a halogen atom, particularly chlorine or bromine, to produce the glycidic ester of the formula (II):

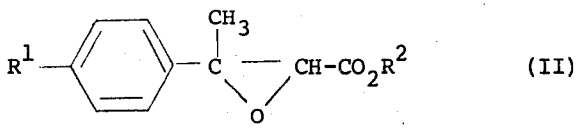

wherein $R^1$ and $R^2$ have the same meanings as defined above. The reaction of the acetophenone derivative of the formula (VIII) with the α-haloacetate of the formula (IX) may be carried out according to a known method of Darzen's condensation.

If the 2-(4-alkylphenyl)-propinic acid of the formula (I) is obtained in the form of the free acid as the final product of the process, the process of this invention may comprise further converting this free acid into the corresponding pharmaceutically acceptable salt (carboxylate) by reacting the free acid with a pharmaceutically acceptable inorganic base such as a sodium potassium calcium or magnesium base. If the 2-(4-alklphenyl)-propionic acid of the formula (I) is yielded in the form of its salt (the carboxylate) as the final product of the process, the process of this invention may comprise further converting this salt into the free acid form in a known manner.

The invention is now illustrated with reference to the following Examples to which the invention is not limited.

EXAMPLE 1

Preparation of methyl 3-methyl-(4-isobutylphenyl)-glycidate

To a stirred mixture of 54.0 g of 4-isobutylacetophenone and 65.0 g of methyl chloroacetate was slowly added 30.0 g of sodium methoxide over 3 hours at a temperature of not more than 5°C under nitrogen atmosphere. The mixture was allowed to come to ambient temperature and stirred overnight. The mixture was then heated to a temperature of 80°–90°C and agitated at this temperature for 1.5 hours. After cooling, the reaction mixture was admixed with ethyl ether, washed with water, dehydrated over anhydrous sodium sulfate and distilled to remove the ether. The residue was distilled to give 61.0 g of methyl 3-(4-isobutylphenyl)-glycidate, B.P. 108°–112°C/0.2 mm Hg. Yield 80.0% (based on the theoretical).

EXAMPLE 2

Preparation of ethyl 3-methyl-3(4-t-butylphenyl)-glycidate

To a stirred mixture of 26.4 g of 4-t-butylacetophenone and 16.2 g of ethyl chloroacetate was slowly added 10.2 g of sodium ethoxide over 30 minutes at a temperature of 10°–15°C. The mixture was allowed to come to room temperature, stirred at room temperature overnight and then heated to 85°C followed by further stirring at this temperature for 1.15 hours. After cooling, the reaction mixture was admixed with ethyl ether, washed with water, dried over anhydrous magnesium sulfate and distilled to remove the ethyl ether. Distillation of the residue gave 25.0 g of ethyl 3-methyl-3-(4-t-butylphenyl)-glycidate, B.P. 10,°–111°C/0.2 mm Hg. Yield 67% (based on theoretical).

EXAMPLE 3

Synthesis of 2-(4-isobutylphenyl)-propionic acid 108° i. Production of 2-(4-isobutylphenyl)-propionaldehyde and 3-methyl-3-(4-isobutylphenyl)-pyruvic acid Isopropyl 3-methyl-3-(4-isobutylphenyl)-glycidate (5.5 g) was dissolved in 20 ml of glacial acetic acid together with 20 ml of a concentrated hydrochloric acid. The mixture was stirred at room temperature for 1 hour and then heated for 1 hour under reflux and with stirring. The reaction mixture was then concentrated under reduced pressure. A volume of water was added to the residue, which was then extracted with ethyl ether. The ether extract was washed with water and then extracted with aqueous sodium carbonate to elute the acidic substance. The remaining ether extract was again washed with water, dried over anhydrous magnesium sulfate and then distilled under reduced pressure to remove the ether. Distillation of the residue gave 2.1 g of 2-(4-isobutylphenyl)-propionaldehyde, B.P. 76°–77°C/0.2 mm Hg. Yield 55%. Elemental analysis (in the form of the 2,4-dinitrophenylhydrazone):

Calculated for C$_{19}$H$_{22}$O$_4$N$_4$: C 61.61, H 5.99, N 15.13%; Found: C 61.52, H 6.08, N 14.99%.

On the other hand, the aqueous sodium carbonate extract was acidified by addition of hydrochloric acid and then extracted with ethyl ether. The resulting ether solution was washed with water, dried and then distilled under reduced pressure to remove the ether. The crude crystals so obtained were recrystallised from petroleum benzine, affording 1.45 g of 3-methyl-3-(4-isobutylphenyl)-pyruvic acid, M.P. 60.5°–61.8°C. Yield 30% (based on the theoretical).

Elemental analysis: Calculated for $C_{14}H_{18}O_3$: C 71.77, H 7.74%; Found: C 71.50, H 7.77%.

ii. Production of 2-(4-isobutylphenyl)-propionic acid from 2-(4-isobutylphenyl)-propionaldehyde.

To a stirred suspension of 1.4 g of silver oxide in 20 ml of 6% aqueous sodium hydroxide was added dropwise 2.1 g of the 2-(4-isobutylphenyl)-propionaldehyde obtained in the procedure of Example 3(i) over 10 minutes at 60°C with stirring. The mixture was further stirred at 60°C for 15 minutes and then allowed to stand. The precipitate was filtered off and washed with hot water. The filtrate and the washing liquor were combined together, and the insoluble oil was removed by extracting with ethyl ether. The remaining aqueous phase was then extracted with ethyl ether, and the ether extract was washed with water, dried and then distilled under reduced pressure to remove the ether. The crude crystalline product so obtained was recrystallised from petroleum benzine, affording 1.3 g of 2-(4-isobutylphenyl)-propionic acid, M.P. 74.8°–76.5°C. Yield 57% (based on the theoretical).

Elemental analysis: Calculated for $C_{13}H_{18}O_2$: C 75.69, H 8.80%; Found: C 75.59, H 8.69%.

iii. Production of 2-(4-isobutylphenyl)-propionic acid from 3-methyl-3-(4-isobutylphenyl)-pyruvic acid.

3-methyl-3-(4-isobutylphenyl)pyruvic acid (1.45 g) obtained in the process of Example 3(i) was dissolved in 10 ml of an aqueous solution of 8% sodium hydroxide, and to the solution was added dropwise 0.9 ml of 30% aqueous hydrogen peroxide with ice-cooling and stirring. The mixture was allowed to come to room temperature and then further stirred overnight at room temperature. The reaction mixture was then acidified by addition of hydrochloric acid and extracted with ethyl ether. The ether extract was washed with water, dried and distilled under reduced pressure to remove the ether. The crude crystalline product so obtained was recrystallised from petroleum benzine, affording 1.1 g of 2-(4-isobutylphenyl)-propionic acid, M.P. 75.2°–76.8°C. Yield 86% (based on the theoretical).

Elemental analysis: Calculated for $C_{13}H_{18}O_2$: C 75.69, H 8.80%; Found: C 75.73, H 8.91%.

EXAMPLE 4

Synthesis of 2-(4-t-butylphenyl)-propionic acid.

i. Production of 2-(4-t-butylphenyl)-propionaldehyde and 3-methyl-3-(4-t-butylphenyl)-pyruvic acid.

Ethyl 3-methyl-3-(4-t-butylphenyl)-glycidate (5.2 g) was dissolved in 20 ml of propionic acid, and the solution was admixed with 20 of 50% sulfuric acid. The mixture was stirred at room temperature for 1 hour and then heated under reflux for 1 hour with stirring. The reaction mixture was concentrated under reduced pressure. A volume of water was added to the residue, which was then extracted with ethyl ether. The ether extract was washed with water and then extracted with aqueous sodium carbonate to separate the acidic substance therefrom. The remaining ether extract was washed with water, dried and distilled under reduced pressure to remove the ether. Distillation of the residue gave 2.0 g of 2-(4-t-butylphenyl)-propionaldehyde, B.P. 70°–71°C/0.2 mm Hg. Yield 53% (based on the theoretical).

Elemental analysis (in the form of the 2,4-dinitrophenylhydrazone): Calculated for $C_{19}H_{22}O_4N_4$: C 61.61, H 5.99, N 15.13%; Found: C 61.58, H 6.03, N 14.98%.

On the other hand, the aqueous sodium carbonate extract was acidified by addition of hydrochloric acid and then extracted with ethyl ether. The ether extract so obtained was washed with water, dried and then distilled under reduced pressure to remove the ether. The crude crystalline product so obtained was recrystallised from petroleum benzine, giving 1.25 g of 3-methyl-3(4-t-butylphenyl)-pyruvic acid, M.P. 88.8°–90.1°C. Yield 27% (based on the theoretical).

Elemental analysis: Calculated for $C_{14}H_{18}O_3$: C 71.77, H 7.74%; Found: C 71.56, H 7.73%.

ii. Production of 2-(4-t-butylphenyl)-propionic acid from 2-(4-t-butylphenyl)-propionaldehyde To a stirred mixture of 2.0 g of 2-(4-t-butylphenyl)-propionaldehyde obtained in the process of Example 4(i) and 20 ml of 20% sulfuric acid was added 2.2 of potassium permanganate over 10 minutes under ice-cooling. The mixture was further stirred for 1 hour at 8°–10°C under ice-cooling. Sodium hydrogen sulfate was added to the mixture and the stirring was continued for 10 minutes. The reaction mixture was extracted with ethyl ether, and the ether extract was then extracted with aqueous potassium carbonate to elute the acidic substance therefrom. The resulting aqueous potassium carbonate extract was made acidic by addition of hydrochloric acid and then extracted with ethyl ether. The ether extract so obtained was washed with water, dried and then distilled under reduced pressure to remove the ether. The crude crystalline product so obtained was recrystallised from petroleum benzine, affording 1.0 g of 2-(4-t-butylphenyl)-propionic acid, M.P. 101°–103°C. Yield 46% (based on the theoretical).

Elemental analysis: Calculated for $C_{13}H_{18}O_2$: C 75.69, H 8.80%; Found: C 75.76, H 8.69%.

iii. Production of 2-(4-t-butylphenyl)-propionic acid from 3-methyl-3-(4-t-butylphenyl)-pyruvic acid.

3-Methyl-3-(4-t-butylphenyl)-pyruvic acid (1.25 g) obtained in the process of Example 4(i) was dissolved in 9 ml of 8% aqueous sodium hydroxide, and to the solution was added dropwise 0.8 ml of 30% aqueous hydrogen peroxide with ice-cooling and stirring. The mixture was allowed to warm to room temperature and then agitated overnight at room temperature. The reaction mixture was acidified by addition of hydrochloric acid and then extracted with ethyl ether. The ether extract was washed with water, dried and then distilled under reduced pressure to remove the ether. The crude crystalline product so obtained was recrystallised from petroleum benzine, affording 0.95 g of 2-(4-t-butylphenyl)-propionic acid, M.P. 102°–103°C. Yield 86% based on the theoretical).

Elemental analysis: Calculated for $C_{13}H_{18}O_2$: C 75.69, H 8.80%; Found: C 75.80, H 8.90%.

The preceeding examples can be repeated with similar success by substituting the generically or specifically described reactants and/or operating conditions of this invention for those used in the preceeding examples.

From the foregoing description, one skilled in the art can acertain the essential characteristics of this invention and, without departing from the spirit and scope thereof, can make various changes and modifications of the invention to adapt it to various usage conditions.

What we claim is:

1. A single-stage process for converting a 3-methyl-3-(4-alkylphenyl)-glycidic acid alkyl ester into a 2-(4-alkylphenyl)-propionaldehyde and a 3-methyl-3-(4-alkylphenyl)-pyruvic acid, which comprises treating:

a. a 3-methyl-3-(4-alkylphenyl)-glycidic acid alkyl ester of the formula

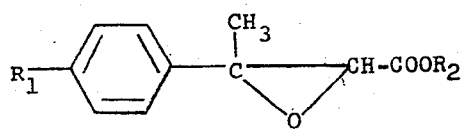

wherein $R_1$ is alkyl of 2–4 carbon atoms and $R_2$ is alkyl of 1–4 carbon atoms, with b. an aqueous mineral acid at an elevated temperature for a period of time sufficient to form reaction products consisting essentially of a 2-(4-alkylphenyl)-propionaldehyde of the formula

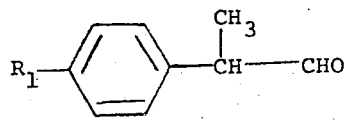

and a 3-methyl-3-(4-alkylphenyl)-pyruvic acid of the formula

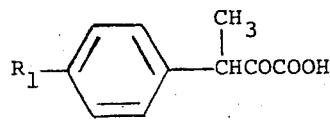

wherein $R_1$ has the above-indicated values.

2. A process according to claim 1, wherein the reaction is effected at a temperature of 80°–140°C.

3. A process according to claim 1, wherein said mineral acid is hydrochloric acid or sulfuric acid.

4. A process according to claim 1, wherein the reactants are dissolved in a lower aliphatic acid.

5. A process according to claim 4, wherein the reaction is effected at a temperatue of 80°–140°C. for about one hour.

6. A process according to claim 1, further comprising oxidizing at least one of said reaction products to form a 2-(4-alkylphenyl)-propionic acid of the formula

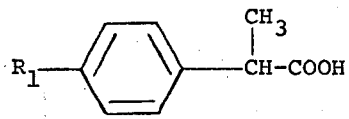

wherein $R_1$ has the above-indicated values, or a pharmaceutically acceptable salt thereof.

7. A process according to claim 6, wherein said propionaldehyde compound is oxidized with silver oxide under alkaline conditions in the presence of an alkali metal hydroxide to form an alkali metal salt of said propionic acid.

8. A process according to claim 6, wherein said propionaldehyde compound is oxidized with acidic aqueous potassium permanganate to form said propionic acid.

9. A process according to claim 6, wherein said pyruvic acid compound is oxidized with aqueous hydrogen peroxide under alkaline conditions in the presence of an alkali metal hydroxide to form an alkali metal salt of said propionic acid compound.

10. A process according to claim 6, wherein:

a. the reaction is effected at a temperature of 80°–140°C. for about one hour to form said reaction products; and b. said propionaldehyde compound and said pyruvic acid compound are separated from each other and oxidized separately to form said propionic acid compound or salt thereof.

* * * * *